US012773682B2

(12) United States Patent
Sanchez

(10) Patent No.: US 12,773,682 B2
(45) Date of Patent: Oct. 27, 2026

(54) METHOD FOR THE PRODUCTION OF BUTANOL USING A TITANIUM-BASED BIMETALLIC HETEROGENEOUS CATALYST

(71) Applicant: TECHCYCLING LLC, San Antonio, TX (US)

(72) Inventor: Ricardo Arreola Sanchez, San Antonio, TX (US)

(73) Assignee: TECHCYCLING LLC, San Antonio, TX (US)

( * ) Notice: Subject to any disclaimer, the term of this patent is extended or adjusted under 35 U.S.C. 154(b) by 579 days.

(21) Appl. No.: 18/042,334

(22) PCT Filed: Aug. 18, 2021

(86) PCT No.: PCT/US2021/046511

§ 371 (c)(1),
(2) Date: Feb. 21, 2023

(87) PCT Pub. No.: WO2022/040318

PCT Pub. Date: Feb. 24, 2022

(65) Prior Publication Data

US 2023/0390739 A1 Dec. 7, 2023

Related U.S. Application Data

(63) Continuation-in-part of application No. 16/997,481, filed on Aug. 19, 2020, now abandoned.

(51) Int. Cl.

*B01J 21/06* (2006.01)
*B01J 6/00* (2006.01)

(Continued)

(52) U.S. Cl.

CPC ............ *B01J 21/063* (2013.01); *B01J 6/001* (2013.01); *B01J 23/8913* (2013.01); *B01J 35/34* (2024.01);

(Continued)

(58) Field of Classification Search

None

See application file for complete search history.

(56) References Cited

U.S. PATENT DOCUMENTS 9,744,523 B2 * 8/2017 Idriss .................... B01J 21/063
11,208,741 B2 * 12/2021 Arai ...................... C09D 11/52

(Continued)

FOREIGN PATENT DOCUMENTS

WO 2016030753 A 3/2016
WO 2019186253 A1 10/2019

*Primary Examiner* — John J Figueroa

(74) *Attorney, Agent, or Firm* — FISHERBROYLES, LLP; Roger L. Browdy

(57) ABSTRACT

The present invention relates to a method for the production of butanol using a titanium-based bimetallic heterogeneous catalyst comprising a support of titanium dioxide doped with cobalt cations and transition metal nanoparticles impregnated in the support. The method describes the production of butanol as a single product, it is environmentally responsible and cost-effective. The present invention also describes a manufacturing process of the titanium-based bimetallic heterogeneous catalyst with enhanced selectivity, activity, and stability, among other advantages.

24 Claims, 11 Drawing Sheets

(51) Int. Cl.

| | |
|---|---|
| ***B01J 23/89*** | (2006.01) |
| ***B01J 35/30*** | (2024.01) |
| ***B01J 35/34*** | (2024.01) |
| ***B01J 35/45*** | (2024.01) |
| ***B01J 35/61*** | (2024.01) |
| ***B01J 35/63*** | (2024.01) |
| ***B01J 35/64*** | (2024.01) |
| ***B01J 35/70*** | (2024.01) |
| ***B01J 35/77*** | (2024.01) |
| ***B01J 37/02*** | (2006.01) |
| ***B01J 37/04*** | (2006.01) |
| ***C07C 29/34*** | (2006.01) |

(52) U.S. Cl.

CPC ............. *B01J 35/393* (2024.01); *B01J 35/45* (2024.01); *B01J 35/613* (2024.01); *B01J 35/615* (2024.01); *B01J 35/633* (2024.01); *B01J 35/647* (2024.01); *B01J 35/70* (2024.01); *B01J 37/0201* (2013.01); *B01J 37/04* (2013.01); *C07C 29/34* (2013.01); *B01J 35/77* (2024.01); *B01J 2235/00* (2024.01); *B01J 2235/15* (2024.01); *B01J 2235/30* (2024.01)

(56) References Cited

U.S. PATENT DOCUMENTS

| | | | | |
|---|---|---|---|---|
| 2010/0038285 | A1* | 2/2010 | Toledo Antonio | B01J 37/0201 208/143 |
| 2012/0043506 | A1 | 2/2012 | Ogata et al. | |
| 2012/0267234 | A1 | 10/2012 | Reece et al. | |
| 2012/0288430 | A1* | 11/2012 | Bello | C01B 3/583 423/247 |
| 2016/0346763 | A1* | 12/2016 | Wahab | B01J 21/063 |
| 2017/0274364 | A1* | 9/2017 | Idriss | B01J 23/72 |
| 2017/0312744 | A1* | 11/2017 | Alghamdi | B01J 23/42 |

* cited by examiner

METHOD FOR THE PRODUCTION OF BUTANOL USING A TITANIUM-BASED BIMETALLIC HETEROGENEOUS CATALYST

RELATED APPLICATIONS

This application claims priority to U.S. application Ser. No. 16/997,481, filed on Aug. 19, 2020. The entire teachings of the above application are incorporated herein by reference.

FIELD OF THE INVENTION

The present invention relates to the production of butanol, and more specifically to the production of butanol using a titanium-based bimetallic heterogeneous catalyst.

BACKGROUND OF THE INVENTION

Demand for biofuels as a substitute for petroleum is expected to increase because of economic and environmental concerns. The common biofuel is ethanol and it has been applied in automobiles with gasoline in different blending proportions. However, ethanol, is not ideal because it has a lower energy density than gasoline and must be mixed with gasoline at a limited concentration range in order to serve as a transportation fuel. Ethanol is also hygroscopic and corrosive, which poses a problem for storage, distribution systems and automotive over time.

On the other hand, butanol also can be used as fuel, which attracted people's attention in recent years. Because of the good properties of high heat value, high viscosity, low volatility, high hydrophobicity, less corrosive, butanol has the potential to be a good fuel in the future. When ethanol is mixed with gasoline (less than 10%), there exists some disadvantages. Firstly, the heating value of ethanol is one sixth of gasoline. The fuel consumption will increase 5% if the engine is not retrofitted. Secondly, acetic acid will be produced during the burning process of ethanol, which is corrosive to the materials of vehicle. Thirdly, ethanol is hydroscopic but poorly soluble in gasoline, so the liquid phase separation may be occurring with high water proportion, provoking damages in automotive. Furthermore, ethanol as fuel cannot be preserved easily and it is more difficult in the process of allocation, storage, transition than that of gasoline due to its high vapor pressure. Compared with ethanol, butanol overcomes the above disadvantages and it shows potential advantages. For example, butanol has higher energy content and higher burning efficiency, which can be used for longer distance. The air to fuel ratio and the energy content of butanol are closer to gasoline. Thus, butanol can be easily mixed with gasoline in any proportion. Butanol is less volatile and explosive, has higher flash point, and lower vapor pressure, which makes it safer to handle and can be shipped through existing fuel pipelines. In addition, butanol can be used directly or blended with gasoline or diesel without any vehicle retrofit.

Butanol can be obtained from the process of fermentation by bacteria (ABE fermentation) as one of the products, in this case called biobutanol. However, the production of butanol by ABE fermentation has several disadvantages related to cost issues, the relatively low-yield and sluggish fermentations, as well as problems caused by end product inhibition and phage infections. Additionally, butanol is produced as only one of several products, so further processes for recovery are necessary to implement. In this sense, according to the atom economy concept, which is an extremely useful tool for evaluating the amount of waste generated by alternative routes to a specific product and one of the 12 "principles of green chemistry" (The Atom Economy-A Search for Synthetic Efficiency; Barry M. Trost; Science 1991, (254), pp 1471-1477), the atom economy for the production of butanol by ABE fermentation is very poor. Atom economy is calculated by dividing the molecular weight of the desired product by the sum total of the molecular weights of all substances produced in the stoichiometric equation for the reactions involved.

It is also possible to produce butanol using chemical technologies, such as oxo-synthesis, catalytic hydrogenation of carbon monoxide and aldol condensation. However, these processes use starting materials derived from petrochemicals and are generally expensive and are not environmentally friendly. The efficient production of butanol from plant-derived raw materials, as cereal crops, sugar cane, sugar beet and cellulosic raw materials, would minimize greenhouse gas emissions and would represent an advance in the art if their atom economy also is above 90%.

In this sense, bimetallic catalysts have attracted extensive attention for a wide range of applications in energy production and environmental remediation due to their tunable chemical/physical properties. These properties are mainly governed by several parameters such as compositions of the bimetallic systems, their preparation method, and their morphostructure. In this regard, numerous efforts have been made to develop bimetallic catalysts with specific nanostructures and surface properties because of recent advances in the area of materials chemistry. As an example, patent document WO2019186253A1 describes a catalyst comprising a titanium dioxide support doped with titanium (IV) cations which is impregnated with metal nanoparticles such as gold, cobalt and palladium. This catalyst is used to produce butanol from ethanol. However, the main technical problems of the catalyst described in this patent document are that the metal nanoparticles have low stability as they are deposited on the surface of a reducible oxide; loss of catalytic activity, a weak nanoparticle-support; and high percentages of metal used. Also, during the formation of the catalyst described in patent document WO2019186253A1 urea is used as a precipitation agent.

Considering the drawbacks of the methods found in the prior art for the production of butanol, as described above, there is a need for an environmentally responsible, cost-effective process for the production of butanol as a single product. The present invention addresses this need by providing a method for the production of butanol using a titanium-based bimetallic heterogeneous catalyst with enhanced selectivity, activity, and stability, among other advantages.

OBJECTS OF THE INVENTION

Considering the problems and disadvantages of the prior art mentioned above, it is an object of the present invention to provide a titanium-based bimetallic heterogeneous catalyst with enhanced selectivity, activity, and stability.

Other object of the present invention is to provide a manufacturing process for the preparation of a titanium-based bimetallic heterogeneous catalyst.

Another object of the present invention is to provide a method for the more efficient production of butanol using a titanium-based bimetallic heterogeneous catalyst, with an atom economy above 90%.

It is another object of the present invention to provide a butanol obtained by heterogeneous catalysis to be used as a biofuel with a vapor pressure of less than 1.53 kPa and a purity of at least 96%.

These and other objects are accomplished by a method for the production of butanol using a Titanium-based bimetallic heterogeneous catalyst in accordance with the present invention.

SUMMARY OF THE INVENTION

The present invention relates to a titanium-based bimetallic heterogeneous catalyst comprising a support of titanium dioxide doped with cobalt cations and transition metal nanoparticles impregnated in the support.

Also, the present invention relates to a manufacturing process of a titanium-based bimetallic heterogeneous catalyst comprising the following steps: a) mixing titanium dioxide with a cobalt salt to obtain a support of titanium dioxide doped with cobalt cations; b) adding to the support of titanium dioxide doped with cobalt cations at least one transition metal salt solution to obtain a titanium-based bimetallic heterogeneous catalyst comprising titanium dioxide doped with cobalt cations and transition metal nanoparticles impregnated in the support.

Other aspect of the present invention relates to a method for the production of butanol comprising the step of introducing a feed of ethanol into a reactor which contains a catalyst comprising a support of titanium dioxide doped with cobalt cations and transition metal nanoparticles impregnated in the support.

Another aspect of the present invention relates to a butanol obtained using a heterogeneous catalyst comprising a support of titanium dioxide doped with cobalt cations and transition metal nanoparticles impregnated in the support, wherein the vapor pressure of the butanol is of less than 1.53 kPa and the butanol has a purity of at least 96%.

BRIEF DESCRIPTION OF THE FIGURES

The accompanying figures, which are incorporated into and constitute a part of this specification, illustrate one or more embodiments of the disclosure and, together with the detailed description, serve to explain the principles and implementations of the invention.

DETAILED DESCRIPTION OF THE INVENTION

Figure 1:
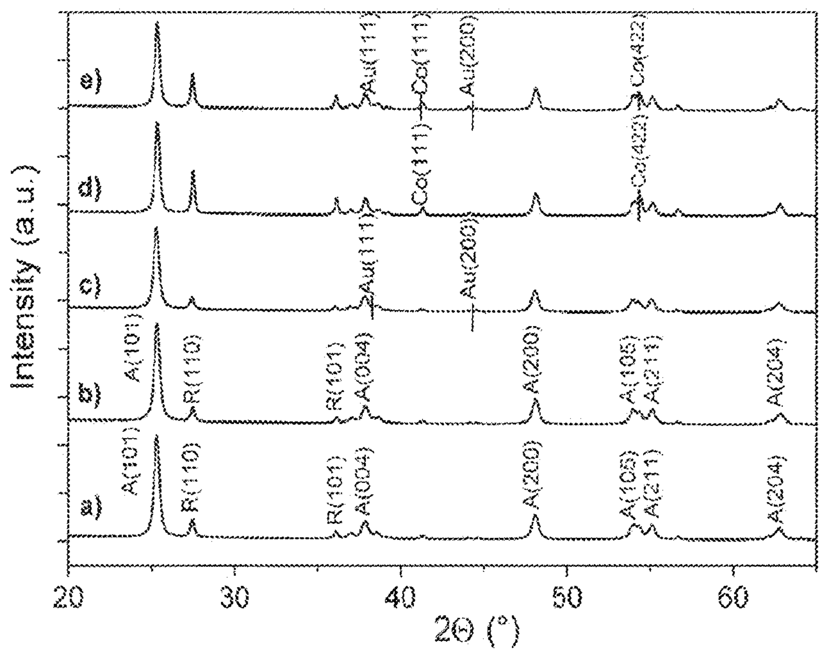
FIG. 1 shows X-ray diffraction pattern of (a) commercial $TiO_2$, (b) Modified-$TiO_2$, (c) Modified-$TiO_2$—Au, (d) Modified-$TiO_2$—Co, and (e) Modified-$TiO_2$—Au—Co according to the principles of the present invention.

The present invention relates to a titanium-based bimetallic heterogeneous catalyst with enhanced selectivity, activity, and stability for the more efficient production of butanol.

For the purpose of this patent application the term "butanol" refers to n-butanol, butyl alcohol or 1-butanol, which corresponds to the following chemical structure (I):

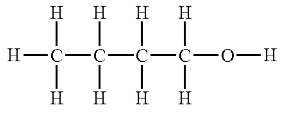

(I)

Also, the term "titanium dioxide" refers to the chemical formulae $TiO_2$, and both the term "titanium dioxide" or the chemical formulae $TiO_2$, could be used indistinctively.

On the other hand, the term "ethanol" includes ethanol produced by any known or future method, including ethanol obtained from biological material processing, which is also known as "bioethanol", and ethanol obtained from oil derivates.

Thus, a first aspect of the present invention relates to a titanium-based bimetallic heterogeneous catalyst comprising a support of titanium dioxide doped with cobalt cations and transition metal nanoparticles impregnated in the support.

In an embodiment of the present invention, the cobalt cations are cobalt, cobalt (II) and cobalt (III) or a mixture thereof. The inclusion of cobalt cations within the titanium dioxide support was found to enrich oxygen vacancies on the support surface to accommodate metallic nanoparticles, which yielded in part the improved catalytic activity, thermal stability and oxygen mobility during aldol condensation. Preferably, the cobalt cations are absorbed into the surface of the support of titanium dioxide.

In another embodiment of the present invention, the transition metal nanoparticles are selected from cobalt (Co) nanoparticles, rhodium (Rh) nanoparticles, gold (Au) nanoparticles, copper (Cu) nanoparticles or a mixture thereof. Preferably the transition metal nanoparticles are a mixture of gold and cobalt nanoparticles, which forms a nanoalloy (Au—Co) in the surface of the titanium dioxide support. It is relevant to mention that metal nanoparticles cobalt (Co) nanoparticles, rhodium (Rh) nanoparticles, gold (Au) nanoparticles, copper (Cu) nanoparticles are transition metals and group 9 and 11 elements.

Also, preferably the transition metal nanoparticles are from approximately 0.1 to 2.0% of the total weight of the titanium-based bimetallic heterogeneous catalyst, and more preferably the transition metal nanoparticles are approximately 0.5 to 1.5% of the total weight of the titanium-based bimetallic heterogeneous catalyst.

Preferably the titanium dioxide support doped with cobalt cations is of a controlled geometry and a low coordination number. Also, preferably the average crystal size of the titanium dioxide support doped with cobalt cations is lower than the average particle size of the common titanium dioxide, and more preferably the crystal size is approximately between nm and 100 nm. This decrease in the crystal size provokes an increase in the surface area, which is also related to the increase of oxygen vacancies.

Additionally, the specific surface area of the titanium dioxide support doped with cobalt cations is higher than the specific surface area of the common titanium dioxide, and more preferably the specific area is approximately between 40 $m^2/g$ and 110 $m^2/g$. This increase in the specific surface area is also related to the incorporation of the cobalt cations into the crystalline structure and the resulting formation of oxygen vacancies on the support surface.

Also, the present invention relates to a manufacturing process of a titanium-based bimetallic heterogeneous catalyst comprising the following steps: a) mixing titanium dioxide with a cobalt salt to obtain a support of titanium dioxide doped with cobalt cations; b) adding to the support of titanium dioxide doped with cobalt cations at least one transition metal salt solution to obtain a titanium-based bimetallic heterogeneous catalyst comprising titanium dioxide doped with cobalt cations and transition metal nanoparticles impregnated in the support.

In an embodiment of the present invention, the step of mixing titanium dioxide with a cobalt salt to obtain a support of titanium dioxide doped with cobalt cations is preferably carried out by a wet precipitation process. After mixing the titanium dioxide with the cobalt salt, the mixture preferably is calcinated, and more preferably it is calcinated at a temperature from 350 to 700° C. under air or hydrogen atmosphere.

The titanium dioxide used in the manufacturing process could be any common titanium dioxide commercially available. Preferably the titanium dioxide is selected from a titanium dioxide with at least 70% of anatase crystalline phase.

The cobalt salt could be selected from any ionic compound containing cobalt. Preferably, the cobalt salt is a phosphate, sulphate, acetate, citrate, chloride or a mixture thereof.

In another embodiment of the present invention, the step of adding to the support of titanium dioxide doped with cobalt cations at least one transition metal salt solution is preferably carried out by a wet precipitation process, and more preferably the wet precipitation process is carried on in water.

Preferably, two transition metal salt solutions are added to the support of titanium dioxide doped with cobalt cations. More preferably, a first transition metal salt solution is added to the support of titanium dioxide doped with cobalt cations to impregnate the support with nanoparticles of a first transition metal, and subsequently a second transition metal salt solution is added to the support of titanium dioxide doped with cobalt cations to impregnate the support with nanoparticles of a second transition metal. Each transition metal salt solution could be selected from a gold (Au) salt solution or a cobalt (Co) salt solution. More preferably, the gold salt solution is $HAuCl_4$ and the cobalt salt solution is phosphate, sulphate, acetate, citrate, chloride or a mixture thereof. In a preferred embodiment of the present invention, after adding the first metal transition salt solution the mixture is dried and calcinated. Then, the second metal transition salt solution is added and the mixture is calcinated again.

One of the advantages of the manufacturing process is that it does not use urea or sodium hydroxide as a precipitating agent since it only uses water as precipitating agent, which results in an easier and simpler process.

Other aspect of the present invention relates to a method for the production of butanol comprising the step of introducing a feed of ethanol into a reactor which contains a catalyst comprising a support of titanium dioxide doped with cobalt cations and transition metal nanoparticles impregnated in the support.

In an embodiment of the present invention, the feed of ethanol is bioethanol which is preferably obtained by sugar fermentation process, wherein the main sources of the sugar required to produce ethanol come from renewable waste materials. These renewable waste materials could be derived from corn, maize and wheat crops, waste straw, willow and popular trees, sawdust, reed canary grass, cord grasses, jerusalem artichoke, myscanthus and sorghum plants. Also, it is preferred that the bioethanol obtained by sugar fermentation process has been purified to achieve at least 96% of purity.

Preferably, the feed of ethanol has a flow rate between 0.001 and 0.1 L/min at the beginning of the reactor, more preferably the feed of ethanol has a flow rate of 0.01 to 0.03 L/min at the beginning of the reactor.

In another embodiment of the present invention, the reactor can be a fixed bed (quartz) reactor with a porous plate. Also, it is preferred that the reactor provides a temperature ramp between 2 and 4° C./minute, more preferably the reactor provides a temperature ramp of 3° C./minute.

Another aspect of the present invention relates to a butanol obtained using a heterogeneous catalyst comprising a support of titanium dioxide doped with cobalt cations and transition metal nanoparticles impregnated in the support, wherein the vapor pressure of the butanol is of less than 1.53 kPa and a purity of at least 96%.

Hereinafter, the present invention will be described in further detail with some examples, but the scope of the present invention is not limited to these examples.

Example 1

An essay was performed to obtain a support of titanium dioxide doped with cobalt cations according to the present invention. For this purpose, 3 g of $TiO_2$ P25 (>99.5%, Aldrich, BET 35-65 $m^2 \cdot g^{-1}$) were suspended in 150 mL of water and homogenized for 30 min. At room temperature and under constant stirring, 200 μL of Cobalt Nitrate Hexahydrate (99.999%, Aldrich) is added dropwise until a final volume of 6 mL is completed. Then the mixture is homogenized at 60° C. for 1 hour. The mixture is placed in a reflux system and heated at 130° C. with constant stirring for 2 hours. The sample is allowed to age at room temperature without stirring. When the material has lost all the water and acquires a metallic appearance, it is crushed in a mortar and calcined under air flow for 2 hours (temperature ramp 5K $min^{-1}$) at 600° C. to obtain the support of titanium dioxide doped with cobalt cations (Co—$TiO_2$).

Example 2

An essay was performed to impregnate the support of titanium dioxide doped with cobalt cations of Example 1 with gold nanoparticles according to the present invention.

The support of titanium dioxide doped with cobalt cations of Example 1 was dried at 100° C. for 12 hours in order to desorb any species that could have been adsorbed on its surface. Then, 1.215 mL ($4.2 \times 10^{-3}$ $mol \cdot L^{-1}$) of $HAuCl_4 \cdot 3H2O$ (99.9%, Aldrich), as a gold salt solution, was mixed in 20 mL of water, and 0.3 g of the support of titanium dioxide doped with cobalt cations of Example 1 was added with stirring. The temperature of the suspension was increased to 80° C. and was kept under constant stirring and protection from light. In this manner, the slow precipitation of $Au^{3+}$ cations was allowed and a local and high increase in pH was avoided. After 12 hours, the material was recovered by centrifugation, washed several times with 50 mL of water and dried at 100° C. In this manner, the support of titanium dioxide doped with cobalt cations of Example 1 was impregnated with gold (Au) nanoparticles.

Example 3

An essay was performed to impregnate the support of titanium dioxide doped with cobalt cations of Example 2 with cobalt nanoparticles, to form a nanoalloy (Au—Co) in its surface and obtain a titanium-based bimetallic heterogeneous catalyst comprising a support of titanium dioxide doped with cobalt cations and transition metal nanoparticles impregnated in the support according to the present invention.

The support of titanium dioxide doped with cobalt cations of Example 2 was dried at 100° C. for 12 hours in order to desorb any species that could have been adsorbed on its surface. Then, 4.05 mL ($4.2 \times 10^{-3}$ $mol \cdot L^{-1}$) of $Co(NO_3)_2 \cdot 6H_2O$ (99.999%, Aldrich), as cobalt salt solution, was mixed in 20 mL of water and homogenized for 15 min at room temperature. Under constant stirring, 0.3 g of the support of titanium dioxide doped with cobalt cations of Example 2 was added. The temperature of the suspension was increased to 80° C. and was kept under constant stirring and protection from light. In this manner, the slow precipitation of Co' cations was allowed and a local and high increase in pH was avoided. The material was recovered by decantation, washed several times with 50 mL of water and dried at 100° C. The resulting material was calcined at 600° C. under air flow with a heating ramp of 5 K $min^{-1}$, maintaining the final temperature for 3 hours. In order to activate the gold and cobalt nanoparticles, the material was treated in a flow of hydrogen at 300° C. for 2 hours with a temperature ramp of 5K $min^{-1}$. The support of titanium dioxide doped with cobalt cations of Example 2 was impregnated with cobalt (Co) nanoparticles.

Example 4

An essay was performed to analyse and compare the crystalline structure of commercial $TiO_2$, the support of titanium dioxide doped with cobalt cations of Example 1 (Modified-$TiO_2$), the support of titanium dioxide doped with cobalt cations impregnated with gold nanoparticles (Modified-$TiO_2$—Au) of Example 2, the support of titanium dioxide doped with cobalt cations impregnated with cobalt nanoparticles (Modified-$TiO_2$—Co) prepared according to the process described in Examples 1 and 3, and the titanium-based bimetallic heterogeneous catalyst comprising a support of titanium dioxide doped with cobalt cations and transition metal nanoparticles impregnated in the support (Modified-$TiO_2$—Au—Co) of Example 3, by X-Ray diffraction.

It is important to preserve the crystalline anatase phase in each of the modification processes and nanoparticle doping, as this phase is relevant to the chemical and thermal stability of the catalyst. For this purpose, two methods of quantification of crystalline phases were used. The first is the RIR method, a semiquantitative method based on reference intensity coefficients and scale factors determined from the phases. The second is the Rietveld method, a highly reliable quantitative method, especially powerful for complex phase mixes that show strong peak overlap due to low concentration.

The composition of commercial $TiO_2$ used was 85.1% anatase and 14.9% rutile.

FIG. 1 shows the X-ray diffraction pattern of the different materials that were analysed. The peaks at $2\theta = 25.3°$, 37.8°, 48.1°, 53.8°, 54.9° and 62.7° (FIG. 1*a*), indicate the presence of the anatase crystalline phase (JCPDS 21-1272) in the commercial $TiO_2$. The peaks at $2\theta = 27.4°$ and 36.0° (FIG. 1*b*), indicate the presence of rutile (JCPDS 21-1276) in the Modified $TiO_2$. The peaks at $2\theta = 38.2°$ and 44.3° (FIG. 1*c*) are attributed to the presence of gold nanoparticles in their face-centered cubic crystalline phase (JCPDS 04-0784) in the Modified $TiO_2$—Au. Reflections at positions $2\theta = 44.22°$ and 51.52° indicate the presence of cobalt in the nanoparticle form and in its oxidized form $2\theta = 36.4°$, 42.3°, 61.4° (FIG. 1*d*) in Modified $TiO_2$—Co.

The intensity of the peaks at $2\theta = 25.3°$ and 27.4° were considered as IA and IR, to calculate the percentage of the anatase phase and rutile phase in each material. As can be seen in Table 1, the relationship between the percentage of anatase is maintained in a greater proportion than that of rutile, a slight decrease in the percentage of the anatase phase between the commercial $TiO_2$ and the Modified $TiO_2$—Au—Co (from 85.1 to 73.0%) confirms that the cation substitution occurred and that this is expected to increase in the number of oxygen vacancies on the surface.

TABLE 1

| | | RIR method | | | Rietveld method | | | |
|---|---|---|---|---|---|---|---|---|
| Commercial $TiO_2$ | | RIR | Intensity | | | Mass | | |
| Reference | Phase | parameter | $I_A/I_R$ | Percentage | Scale | formulae | Volume | Percentage |
| 98-007-6173 | Anatase | 5.269 | 0.962 | 79.2% | 0.026242 | 319.46 | 136.318 | 85.1% |
| 98-006-4987 | Rutile | 3.709 | 0.178 | 20.8% | 0.019976 | 159.73 | 62.473 | 14.9% |
| | | RIR method | | | Rietveld method | | | |
| Modified-$TiO_2$ | | RIR | Intensity | | | Mass | | |
| Reference | Phase | parameter | $I_A/I_R$ | Percentage | Scale | formulae | Volume | Percentage |
| 98-002-4276 | Anatase | 5.120 | 0.961 | 79.2% | 0.026272 | 319.46 | 136.2062 | 87.9% |
| 98-020-2241 | Rutile | 3.783 | 0.155 | 20.8% | 0.015726 | 159.73 | 62.41739 | 12.1% |
| | | RIR method | | | Rietveld method | | | |
| Modified-$TiO_2$-Au | | RIR | Intensity | | | Mass | | |
| Reference | Phase | parameter | $I_A/I_R$ | Percentage | Scale | formulae | Volume | Percentage |
| 98-009-3098 | Anatase | 5.079 | 0.965 | 79.5% | 0.021434 | 319.46 | 136.2459 | 88.2% |
| 98-008-2083 | Rutile | 3.288 | 0.161 | 20.5% | 0.012541 | 159.73 | 62.44517 | 11.8% |
| | | RIR method | | | Rietveld method | | | |
| Modified-$TiO_2$-Co | | RIR | Intensity | | | Mass | | |
| Reference | Phase | parameter | $I_A/I_R$ | Percentage | Scale | formulae | Volume | Percentage |
| 98-002-4277 | Anatase | 5.269 | 0.959 | 62.6% | 0.019784 | 319.46 | 136.2579 | 70.5% |
| 98-002-4277 | Rutile | 3.625 | 0.395 | 37.4% | 0.03613 | 159.73 | 62.50317 | 29.5% |
| | | RIR method | | | Rietveld method | | | |
| Modified-$TiO_2$-Au-Co | | RIR | Intensity | | | Mass | | |
| Reference | Phase | parameter | $I_A/I_R$ | Percentage | Scale | formulae | Volume | Percentage |
| 98-002-4276 | Anatase | 5.120 | 0.929 | 64.1% | 0.019029 | 319.46 | 136.2029 | 73.0% |
| 98-002-4277 | Rutile | 3.625 | 0.368 | 35.9% | 0.030571 | 159.73 | 62.56346 | 27.0% |

Table 2 shows the calculation of the crystal size of commercial $TiO_2$ and Modified-$TiO_2$. In order to perform the crystal size calculation, the Scherrer equation was used. The crystal size of the commercial $TiO_2$ was larger (19.8 nm) than that of the Modified-$TiO_2$ (17.3 nm). The decrease in the crystal size is related to the increase in the surface area-volume, confirming the presence of oxygen vacancies available on the surface of the Modified-$TiO_2$.

TABLE 2

| Material | Crystal size (nm) |
|---|---|
| Commercial $TiO_2$ | 19.8 |
| Modified-$TiO_2$ | 17.3 |

Example 5

An essay was performed to analyse and compare the specific surface area (BET) and the porous size distribution (BJH) of commercial $TiO_2$, the support of titanium dioxide doped with cobalt cations of Example 1 (Modified-$TiO_2$), and the titanium-based bimetallic heterogeneous catalyst comprising a support of titanium dioxide doped with cobalt cations and transition metal nanoparticles impregnated in the support (Modified-$TiO_2$—Au—Co) of Example 3.

Figure 2:
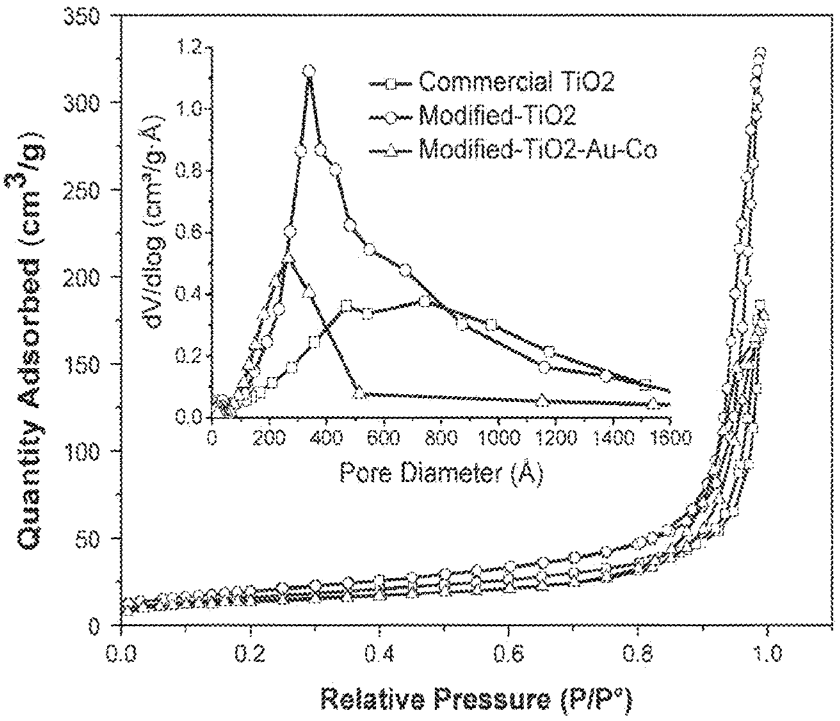
FIG. 2 shows the $N_2$ adsorption-desorption isotherms of Commercial $TiO_2$, Modified-$TiO_2$ and Modified-$TiO_2$—Au—Co according to the principles of the present invention.

In FIG. 2, the $N_2$ adsorption-desorption isotherms of the Commercial $TiO_2$, Modified-$TiO_2$ and Modified-$TiO_2$—Au—Co are shown. For the commercial $TiO_2$ a type IV isotherm is observed with a hysteresis loop that adjusts to mesoporous type materials. The isotherms of the Modified-$TiO_2$ and Modified-$TiO_2$—Au—Co show a type IV curve, with hysteresis. The BJH pore size distribution (box in FIG. 2) for the Commercial $TiO_2$ is 65 nm, for the Modified-$TiO_2$ is 35 nm, and for the Modified-$TiO_2$—Au—Co is 28 nm, confirming the distribution pore size of mesoporous type materials.

In Table 3, the textural properties of the Commercial $TiO_2$, Modified-$TiO_2$ and Modified-$TiO_2$—Au—Co are listed. The specific surface area of the Modified-$TiO_2$ is greater (64.95 $m^2 g^{-1}$) than that of the Commercial $TiO_2$ (56.87 $m^2 g^{-1}$). Both the pore diameter and the pore volume increase for the Modified-$TiO_2$—Au—Co. This can be attributed to the incorporation of cobalt cations within the structure of $TiO_2$ and the formation of oxygen vacancies.

TABLE 3

| Material | Specific surface area ($m^2$/g) | Pore volume ($cm^3$/g) | Pore diameter (nm) |
|---|---|---|---|
| Commercial $TiO_2$ | 56.87 | 0.29 | 19 |
| Modified-$TiO_2$ | 64.95 | 0.39 | 22 |
| Modified-$TiO_2$—Au—Co | 53.17 | 0.31 | 21 |

Example 6

An essay was performed to analyse and compare the temperature-programmed desorption (TPD) of commercial $TiO_2$, the support of titanium dioxide doped with cobalt cations of Example 1 (Modified-$TiO_2$), the support of titanium dioxide doped with cobalt cations impregnated with gold nanoparticles (Modified-$TiO_2$—Au) of Example 2, the support of titanium dioxide doped with cobalt cations impregnated with cobalt nanoparticles (Modified-$TiO_2$—Co) prepared according to the process described in Examples 1 and 3, and the titanium-based bimetallic heterogeneous catalyst comprising a support of titanium dioxide doped with cobalt cations and transition metal nanoparticles impregnated in the support (Modified-$TiO_2$—Au—Co) of Example 3.

Figure 3:
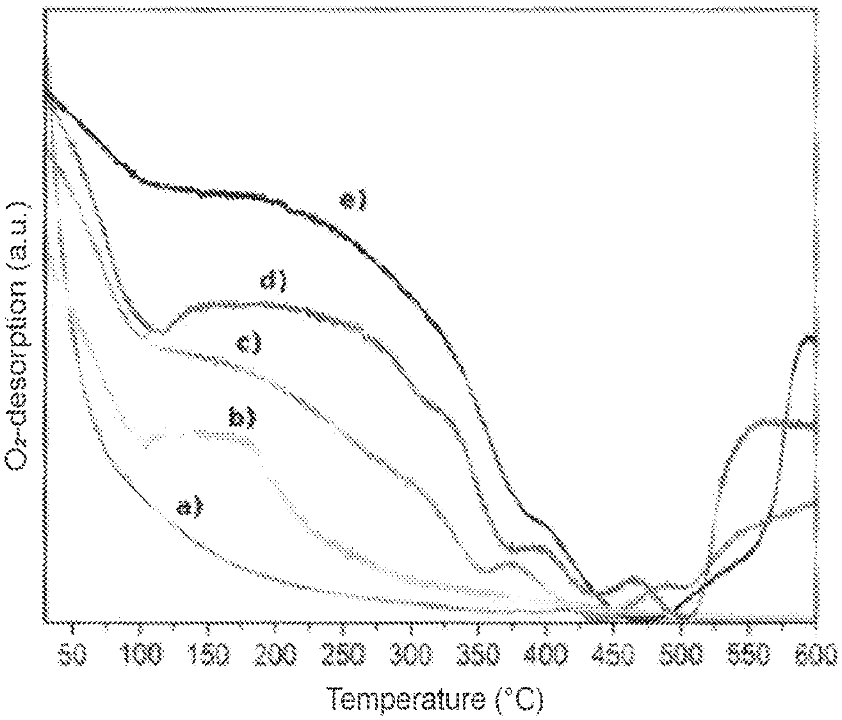
FIG. 3 shows the results of the temperature-programmed desorption (TPD) analysis of Commercial $TiO_2$ (a), Modified-$TiO_2$ (b), Modified-$TiO_2$—Au (c), Modified-$TiO_2$—Co (d), and Modified-$TiO_2$—Au—Co (e) according to the principles of the present invention.

In FIG. 3, the results of the TPD analysis of Commercial $TiO_2$ are indicated with the letter (a), the results of the TPD analysis of the Modified-$TiO_2$ are indicated with the letter (b), the results of the TPD analysis of Modified-$TiO_2$—Au are indicated with the letter (c), the results of the TPD analysis of Modified-$TiO_2$—Co are indicated with the letter (d), and the results of the TPD analysis of Modified-$TiO_2$—Au—Co are indicated with the letter (e).

The results of the TPD analysis as shown in FIG. 3 are relevant since they reveal that the introduction of cobalt cations into the structure of $TiO_2$ generates new 02 adsorption sites and increases the desorption and activation capacity of 02 up to 3 times more in the Modified-$TiO_2$—Au—Co material. This is directly related to the capacity of the Modified-$TiO_2$—Au—Co as a catalyst to promote oxygen mobility within the material, which is important for the transformation of ethanol into butanol in the present invention.

Example 7

An essay was performed to measure the particle size of the titanium-based bimetallic heterogeneous catalyst comprising a support of titanium dioxide doped with cobalt cations and transition metal nanoparticles impregnated in the support (Modified-$TiO_2$—Au—Co) of Example 3.

Figure 4:
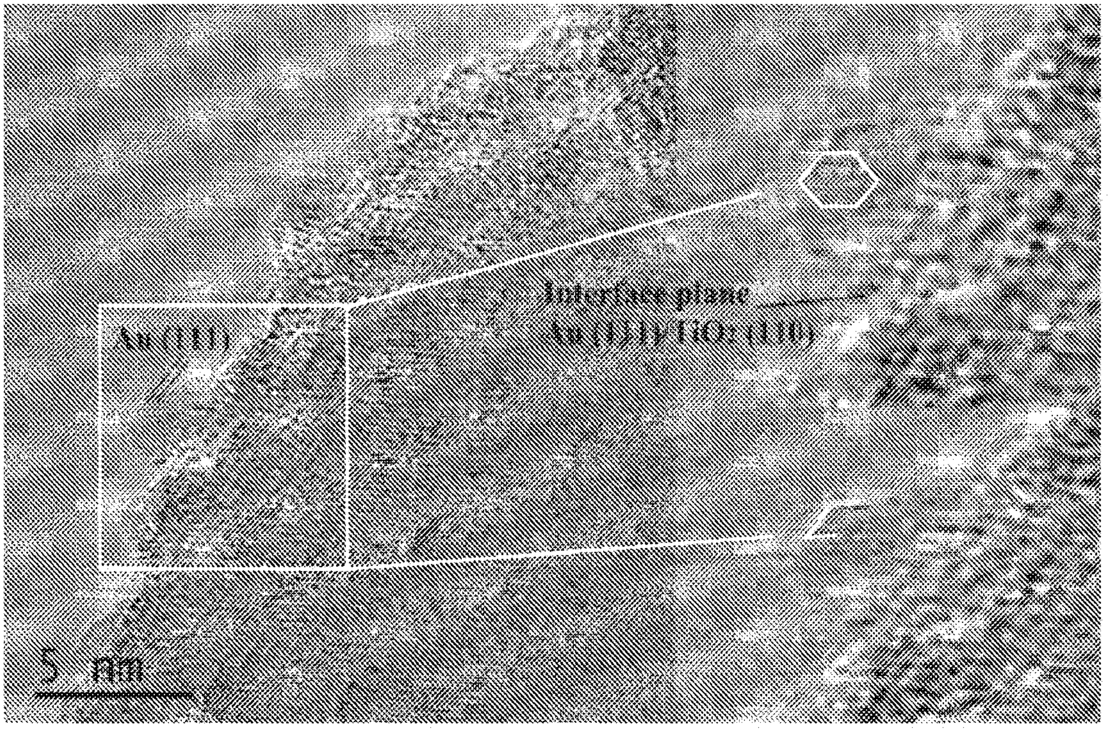
FIG. 4 shows the HRTEM micrograph of the Modified-$TiO_2$—Au—Co according to the principles of the present invention.
Figure 5:
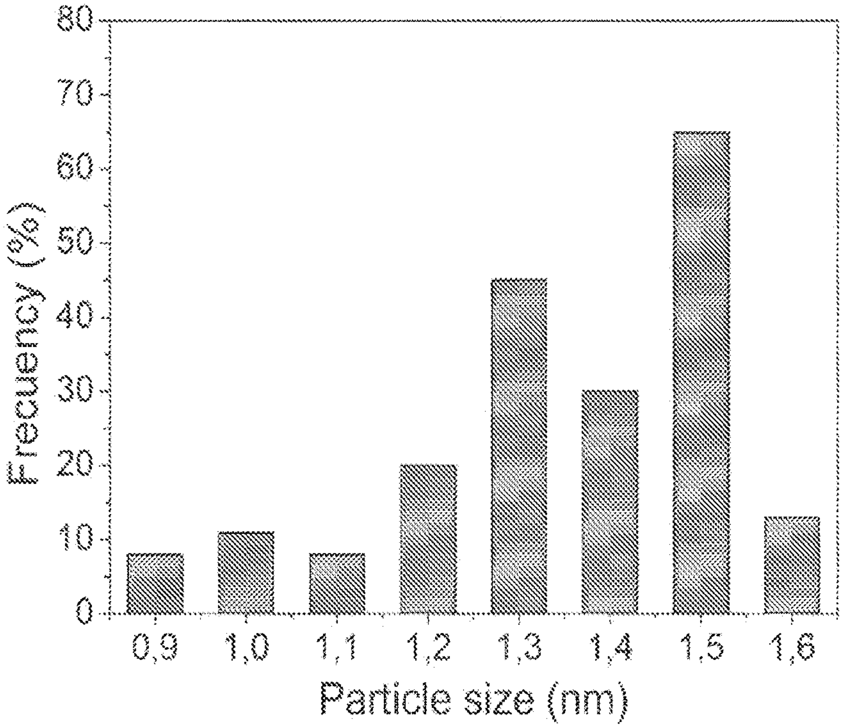
FIG. 5 shows a frequency histogram of the particle size of the Modified-$TiO_2$—Au—Co according to the principles of the present invention.

In FIG. 4, the HRTEM micrograph of the Modified-$TiO_2$—Au—Co is observed. Nanoparticles of sizes between 0.9 and 1.6 nm (average of a count of 500 particles) are observed. The nanoparticles are perfectly faceted and have the unique shape of a truncated octahedron, exposing the Au plane (111) and (100), epitaxially anchored to the anatase crystalline phase (112) of the Modified-$TiO_2$—Au—Co and with a flat interface. The nanoparticles have a high presence of planes so they directly affect the low coordination of the particle and its high catalytic activity. The atomic configuration of the surface favours the deposition of the gold nanoparticle in the plane (111), over the oxygen vacancies layer of the $TiO_2$. No sintering effects are observed for these nanoparticles when deposited on the Modified-$TiO_2$ and when tested in catalytic cycles at temperatures of 1000° C. (see FIG. 12 discussed in Example 12). This confirms that the manufacturing process is efficient to generate chemically and thermally stable nanoparticles, with a highly reactive orientation in the aldol condensation reaction of ethanol to butanol. The optical, electrical, electromagnetic and conduction properties are linked to the particle size, since nanoparticles with diameters less than 3 nm have a greater adsorption of the electromagnetic spectrum, greater ferromagnetism and a lower chemical coordination, increasing their activity and chemical selectivity during a process. FIG. 5 shows a frequency histogram of the particle size of the Modified-$TiO_2$—Au—Co.

Example 8

An essay was performed to assess the aldol condensation from ethanol to butanol using the titanium-based bimetallic heterogeneous catalyst comprising a support of titanium dioxide doped with cobalt cations and transition metal nanoparticles impregnated in the support (Modified-$TiO_2$—Au—Co) of Example 3, according to the present invention. Also, for the purpose of comparing catalytic performance, it was also tested the aldol condensation from ethanol to butanol using commercial $TiO_2$, the support of titanium dioxide doped with cobalt cations of Example 1 (Modified-$TiO_2$), a catalyst comprising a support of titanium dioxide doped with titanium (IV) cations (ModifiedTiIV—$TiO_2$) according to the prior art, and a catalyst comprising a support of titanium dioxide doped with titanium (IV) cations and gold nanoparticles (ModifiedTiIV—$TiO_2$—Au) according to the prior art.

For assessing Modified-$TiO_2$—Au—Co, 150 mg of Modified-$TiO_2$—Au—Co were weighed and sieved, the Modified-$TiO_2$—Au—Co was compressed and inserted into a fixed bed quartz reactor with a porous catalytic bed. The reactor is coupled in its inflow to a 0.01 to 0.03 L/min ethanol feed system (previously obtained from biomass and reaching a degree of purity of 96%) and subjected to a temperature ramp inside an electric furnace controlled with increments of 3° C. per minute. Outgoing gases were analyzed online with a gas chromatograph (Perkin Elmer Clarus 580) equipped with a flame ionization detector (FID). A TRB5MS capillary column (30 m, 0.25 mm) was used as the stationary phase. Compound identification was performed using commercial standards and confirmed by GCMS (Shimadzu QP2010) using the same column and methodology as in the GCFID. Conversions were calculated from the ethanol concentration at the inlet and outlet of the reactor. The selectivity was calculated using the economy of the atom, relating the concentration between the desired product (butanol) and the concentration of all the identified reaction products (acetaldehyde, acetic acid, butanal, crotonaldehyde, crotyl alcohol, diethyl ether, ethyl acetate, ethylene, methane, 1-hexanol, 1-octanol, 1,3-butadiene, 2-ethylbutanol and 2-ethylhexanol) considering the carbon atoms of each component. Carbon balances were verified by comparing the total amount of carbon atoms at the inlet and outlet of the reactor, considering the identified products.

Figure 6:
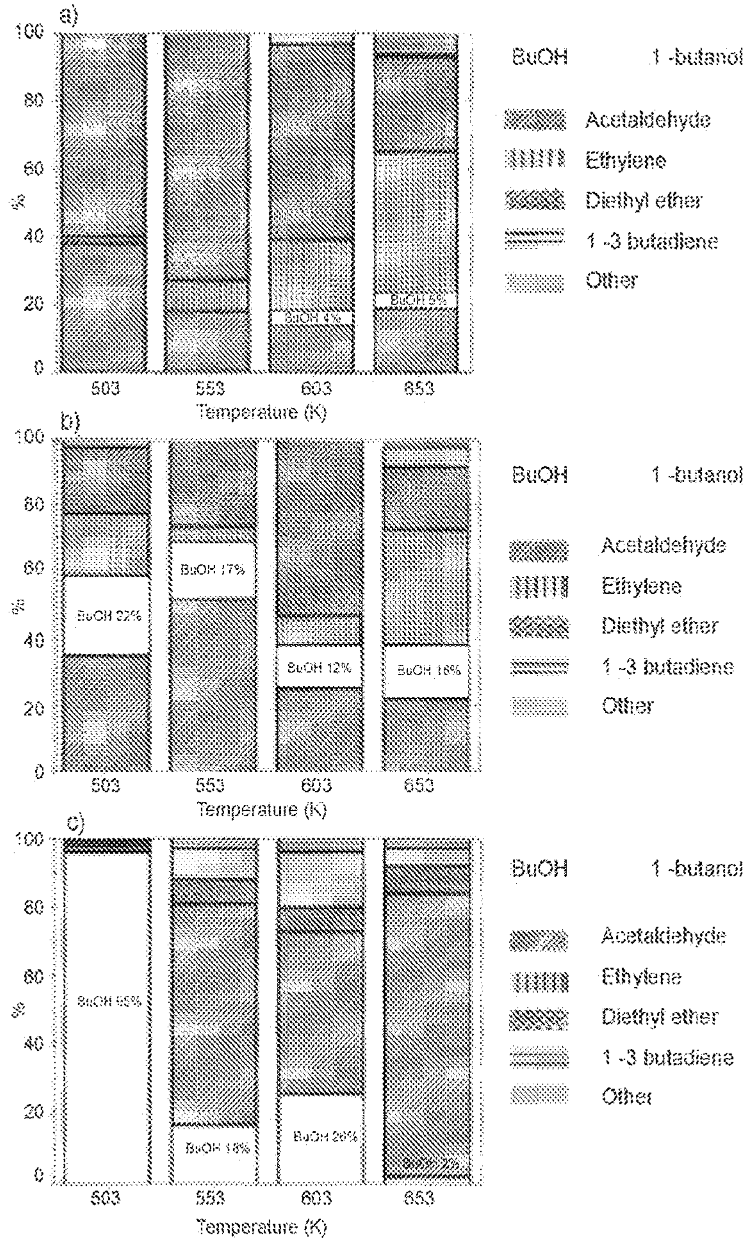
FIG. 6 shows the products during the aldol condensation from ethanol to butanol using as catalyst (a) Commercial $TiO_2$, (b) Modified-$TiO_2$, or (c) Modified-$TiO_2$—Au—Co according to the principles of the present invention.

In this regard FIG. 6 shows the products during the aldol condensation from ethanol to butanol using as catalyst (a)

Commercial $TiO_2$, (b) Modified-$TiO_2$, or (c) Modified-$TiO_2$—Au—Co according to the principles of the present invention.

On the other hand, tests of the Modified TiIV—$TiO_2$—Au were performed under the same conditions, but with an injection of Hydrogen at the inlet of the catalytic reactor of 0.02 L/min (STP) ($H_2$/He). It is important to note that the injection of Hydrogen is used in this case because the ModifiedTiIV—$TiO_2$—Au is not capable of promoting hydrogen to generate chemical balance, as in the case of the catalyst of the present invention. 150 mg of the ModifiedTiIV—$TiO_2$—Au were weighed and sieved at 250-355 μm, the ModifiedTiIV—$TiO_2$—Au is compressed and inserted into a fixed bed quartz reactor with a porous catalytic bed. The reactor is coupled in its inflow to a 0.02 L/min ethanol feed system (previously obtained from biomass and reaching a degree of purity of 96%) and subjected to a temperature ramp inside an electric furnace controlled with increments of 3° C. per minute. Outgoing gases were analyzed online with a gas chromatograph (HP6890 Plus) equipped with a flame ionization detector (FID). A TRB5MS capillary column (30 m, 0.25 mm) was used as the stationary phase. Component identification was performed using commercial standards and confirmed by GCMS (Shimadzu QP2010) using the same column and methodology as in the GCFID. Conversions were calculated from the ethanol concentration at the inlet and outlet of the reactor. The selectivity was calculated using the economy of the atoms, relating the concentration between the desired product (butanol) and the concentration of all the identified reaction products (acetaldehyde, acetic acid, butanal, crotonaldehyde, crotyl alcohol, diethyl ether, ethyl acetate, ethylene, methane, 1-hexanol, 1-octanol, 1,3-butadiene, 2-ethylbutanol and 2-ethylhexanol) considering the carbon atoms of each component. Carbon balances were verified by comparing the total amount of carbon atoms at the inlet and outlet of the reactor, considering the identified products. The "percent atom economy" was calculated as follows:

% Atom Economy=(FW of atoms utilized/FW of all reactants)×100=97.98%.

Figure 7:
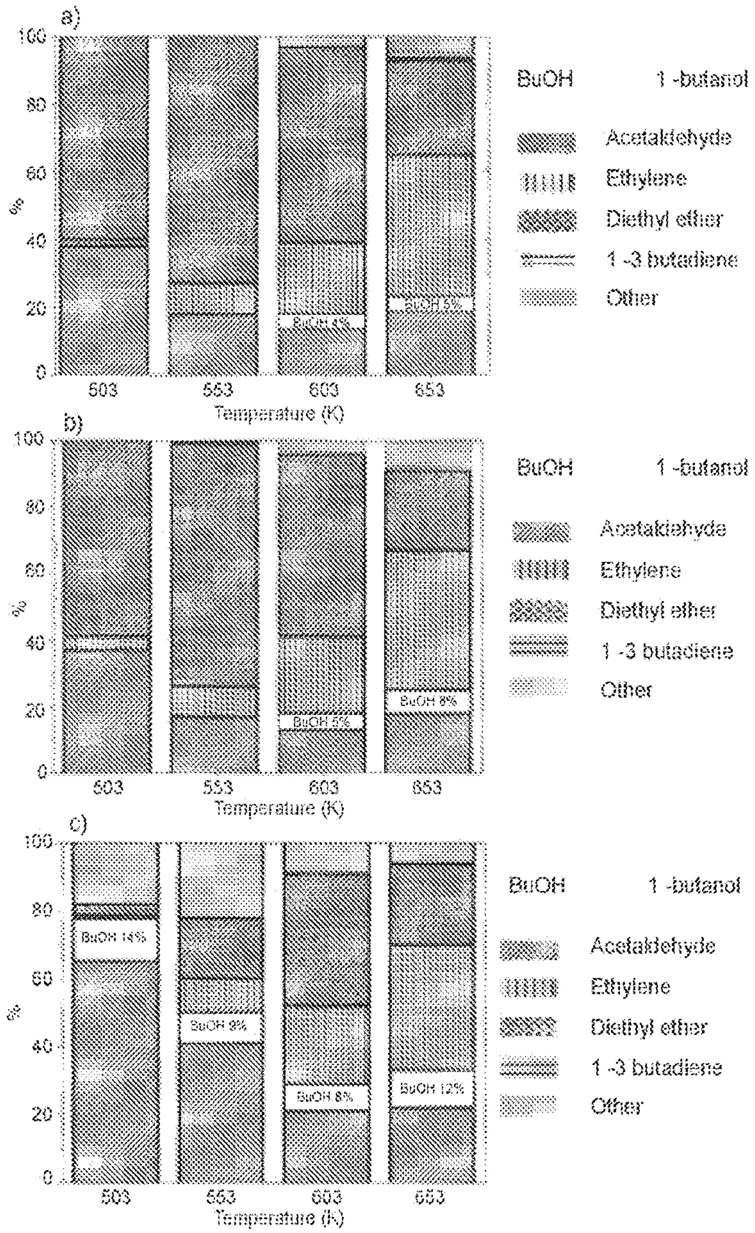
FIG. 7 shows the products during the aldol condensation from ethanol to butanol using as catalyst (a) Commercial $TiO_2$, (b) Modified-TiIV—$TiO_2$, or (c) Modified-TiIV—$TiO_2$—Au according to the principles of the present invention.

In this regard FIG. 7 shows the products during the aldol condensation from ethanol to butanol using as catalyst (a) Commercial $TiO_2$, (b) Modified-TiIV—$TiO_2$, or (c) Modified-TiIV—$TiO_2$—Au according to the principles of the present invention.

In Table 4 it is summarized the catalytic activity in the aldol condensation from ethanol to butanol at different temperatures.

TABLE 4

| Temperature (K) | Commercial $TiO_2$ | ModifiedTiIV-$TiO_2$ | Modified-$TiO_2$ | ModifiedTiIV-$TiO_2$—Au | Modified-$TiO_2$—Au—Co |
|---|---|---|---|---|---|
| 523 K | 0% | 0% | 24% | 12.8% | 96% |
| 623 K | 4% | 3% | 13% | 8% | 26% |

The Modified-$TiO_2$—Au—Co, according to the present invention, has the highest catalytic activity in the aldol condensation from ethanol to butanol.

Example 9

An essay was performed to analyse and compare the magnetic properties of commercial $TiO_2$, the support of titanium dioxide doped with cobalt cations of Example 1 (Modified-$TiO_2$), the support of titanium dioxide doped with cobalt cations impregnated with gold nanoparticles (Modified-$TiO_2$—Au) of Example 2, the support of titanium dioxide doped with cobalt cations impregnated with cobalt nanoparticles (Modified-$TiO_2$—Co) prepared according to the process described in Examples 1 and 3, and the titanium-based bimetallic heterogeneous catalyst comprising a support of titanium dioxide doped with cobalt cations and transition metal nanoparticles impregnated in the support (Modified-$TiO_2$—Au—Co) of Example 3. The magnetic properties were obtained using a vibrating sample magnetometer (VSM) and compared to a catalyst comprising a support of titanium dioxide doped with titanium (IV) cations and gold nanoparticles (ModifiedTiIV—$TiO_2$—Au) according to the prior art.

Figure 8:
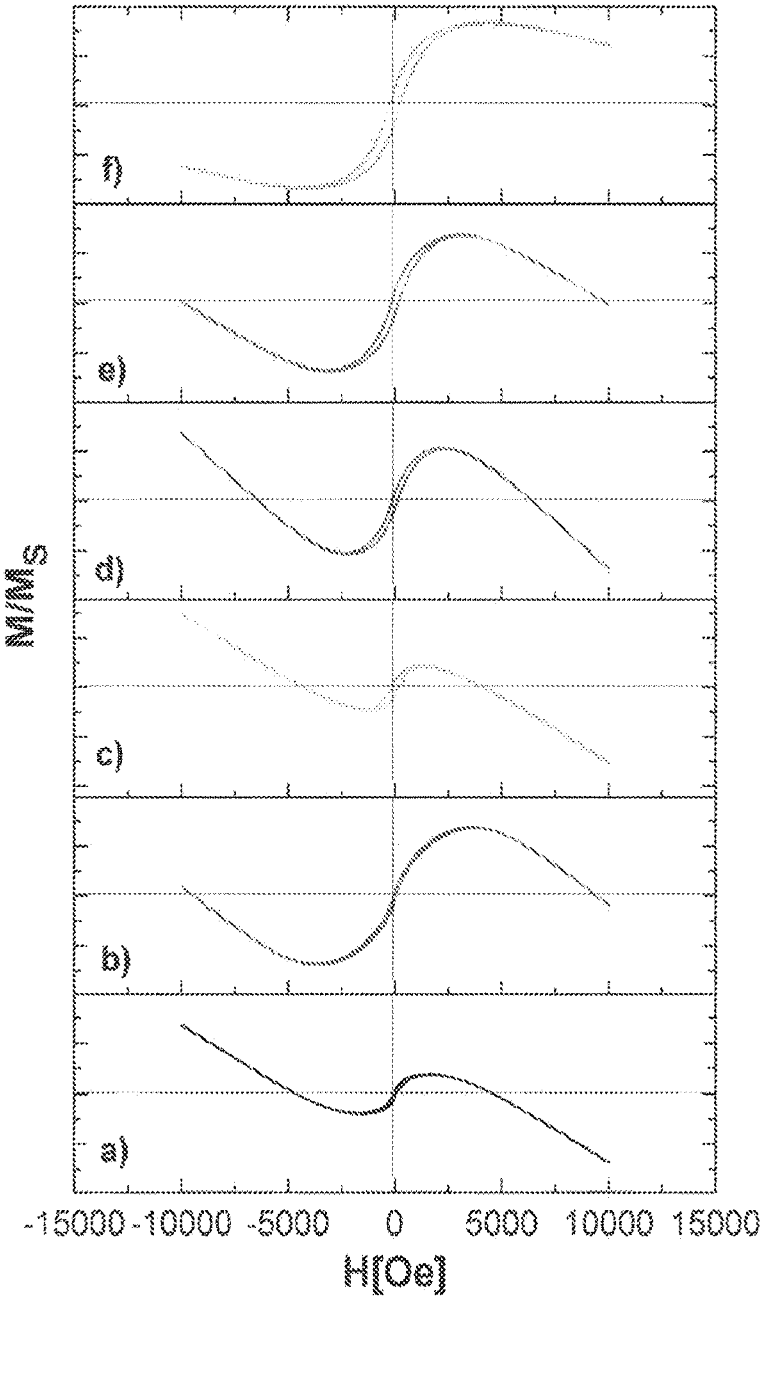
FIG. 8 shows the saturation in the magnetization curve of commercial $TiO_2$ (a), Modified-$TiO_2$ (b), ModifiedTiIV—$TiO_2$—Au (c) of the prior art, Modified-$TiO_2$—Au (d), Modified-$TiO_2$—Co (e), and Modified-$TiO_2$—Au—Co (f) according to the principles of the present invention.

FIG. 8(*a*) shows the saturation in the magnetization curve of commercial $TiO_2$ as a low superparamagnetic material. The saturation in the magnetization curve of Modified-$TiO_2$ in FIG. 8(*b*) shows a slight increase in superparamagnetism in relation to the commercial $TiO_2$. The magnetic properties of ModifiedTiIV—$TiO_2$—Au in FIG. 8(*c*) features a high superparamagnetic material. The saturation in the magnetization curve of Modified-$TiO_2$—Au in FIG. 8(*d*) shows a hysteresis loop, characteristic of a low ferromagnetic material. The saturation in the magnetization curve of Modified-$TiO_2$—Co in FIG. 8(*e*) shows a hysteresis loop slightly stronger than Modified-$TiO_2$—Au in FIG. 8(*d*), characteristic of a medium ferromagnetic material. The saturation in the magnetization curve of the Modified-$TiO_2$—Au—Co in FIG. 8(*f*) shows a hysteresis loop which is a characteristic of a high ferromagnetic material. In this regard, it is important to note that the magnetic fields generated by the ferromagnetic particles (gold and cobalt nanoparticles) deposited on the surface of the modified support (Modified-$TiO_2$) are responsible for fixing substrates (ethanol-ethanol), transferring charge density to the support and activating the Mars Van Krevelen cycle (oxygen mobility towards the surface of the modified support) to increase the efficiency in the aldol condensation reaction of ethanol to butanol.

In Table 5 it is summarized the magnetic properties of the different material that were obtained.

TABLE 5

| Material | Magnetic Properties |
|---|---|
| Commercial $TiO_2$ | Low superparamagnetic |
| Modified-$TiO_2$ | Medium superparamagnetic |
| ModifiedTiIV-$TiO_2$—Au | High superparamagnetic |
| Modified-$TiO_2$—Au | Low ferromagnetic |
| Modified-$TiO_2$—Co | Medium ferromagnetic |
| Modified-$TiO_2$—Au—Co | High ferromagnetic |

Example 10

An essay was performed to analyse and compare the optic properties of commercial $TiO_2$, the support of titanium dioxide doped with cobalt cations of Example 1 (Modified-$TiO_2$), the support of titanium dioxide doped with cobalt cations impregnated with gold nanoparticles (Modified-$TiO_2$—Au) of Example 2, the support of titanium dioxide doped with cobalt cations impregnated with cobalt nanoparticles (Modified-$TiO_2$—Co) prepared according to the process described in Examples 1 and 3, and the titanium-based bimetallic heterogeneous catalyst comprising a support of titanium dioxide doped with cobalt cations and transition metal nanoparticles impregnated in the support (Modified-$TiO_2$—Au—Co) of Example 3. The optic properties were obtained by surface plasmon resonance (SPR) in comparison with a catalyst comprising a support of titanium dioxide doped with titanium (IV) cations and gold nanoparticles (ModifiedTiIV—$TiO_2$—Au) according to the prior art.

Figure 9:
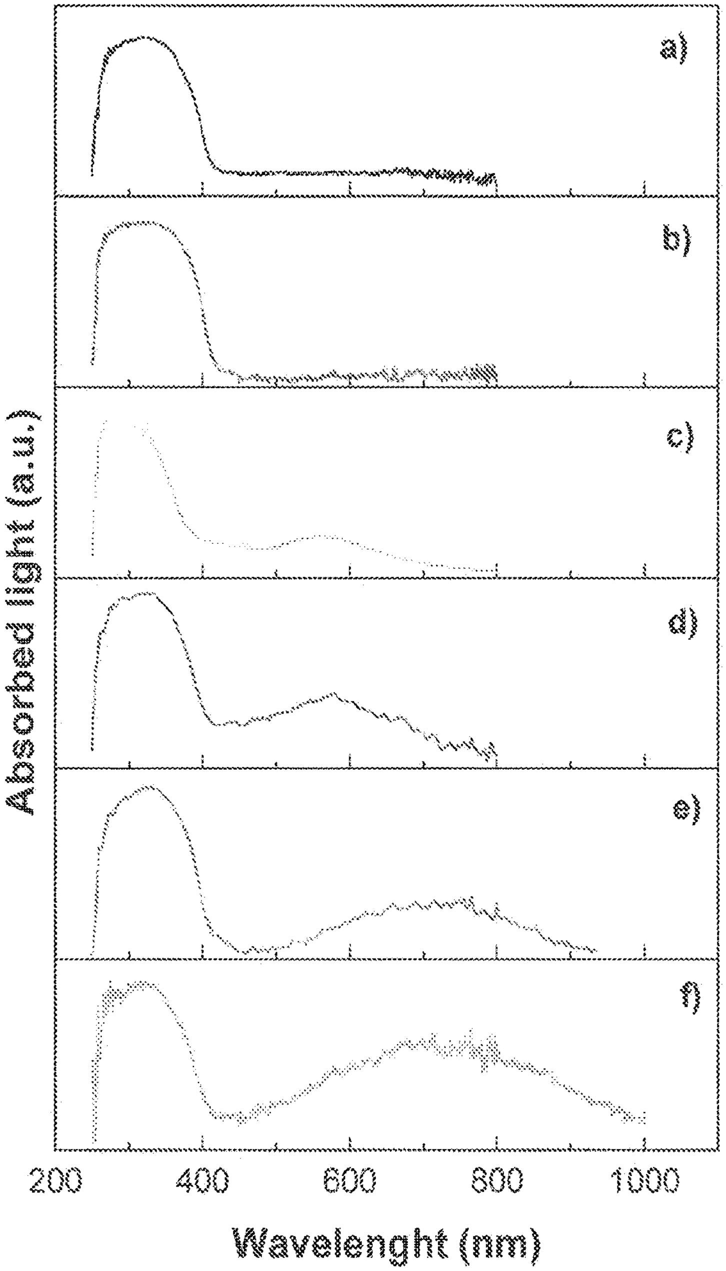
FIG. 9 shows the absorption spectrum of Commercial $TiO_2$ (a), Modified-$TiO_2$ (b), ModifiedTiIV—$TiO_2$—Au (c) of the prior art, Modified-$TiO_2$—Au (d), Modified-$TiO_2$—Co (e) and Modified-$TiO_2$—Au—Co (f) according to the principles of the present invention.

In FIG. 9(*a*), the absorption spectrum of Commercial $TiO_2$ is observed and it can be seen that there is absorbance at low wavelengths (250-400 nm ultraviolet region). In FIG. 9(*b*) the absorption spectrum of Modified-$TiO_2$ shows no significant changes in absorbance with respect to Commercial $TiO_2$. In FIG. 9(*c*) the absorption spectrum of ModifiedTiIV—$TiO_2$—Au shows the typical absorption of $TiO_2$ in the ultraviolet region and a slight absorption in the visible part, corresponding to the collective oscillation of the electrons of the gold surface plasmon. In FIG. 9(*d*) the absorption spectrum of Modified-$TiO_2$—Au shows an absorption band at 562 nm (in addition to the absorption in the ultraviolet region of Modified-$TiO_2$) which is associated to the formation of the dipole of the conduction electrons of the gold nanoparticles. In FIG. 9(*e*) the absorption spectrum of Modified-$TiO_2$—Co shows an absorption band slightly displaced at higher wavelengths. In FIG. 9(*f*) the absorption spectrum of Modified-$TiO_2$—Au—Co shows absorbances at low and high wavelengths of the entire electromagnetic spectrum. This absorption of the entire electromagnetic spectrum of Modified-$TiO_2$—Au—Co contributes to the oscillation of the electrons in the conduction band of the nanoparticles, favouring the mobility of electrons in the oxidation reactions and reduction and activation of the Mars Van Krevelen cycle for the aldol condensation reaction of ethanol to butanol.

Table 6 summarizes the electromagnetic absorption of the different material that were assessed.

TABLE 6

| Material | Electromagnetic absorption |
|---|---|
| Commercial $TiO_2$ | UV 200-400 nm |
| Modified-$TiO_2$ | UV near blue 200-420 nm |
| Modified TiIV-$TiO_2$-Au | UV 200-400 nm |
| | Vis 500-650 nm |
| Modified-$TiO_2$-Au | UV 200-400 nm |
| | Vis 400-700 nm |
| | IR 700-800 nm |
| Modified-$TiO_2$-Co | UV 200-400 nm |
| | Vis 400-700 nm |
| | IR 700-900 nm |
| Modified-$TiO_2$-Au-Co | UV 200-400 nm |
| | Vis 400-700 nm |
| | IR 700-1000 nm |

Example 11

An essay was performed to compare the structural differences between commercial $TiO_2$ and the support of titanium dioxide doped with cobalt cations of Example 1 (Modified-$TiO_2$). This essay was performed using X-ray Photoelectron Spectroscopy (XPS).

Figure 10:
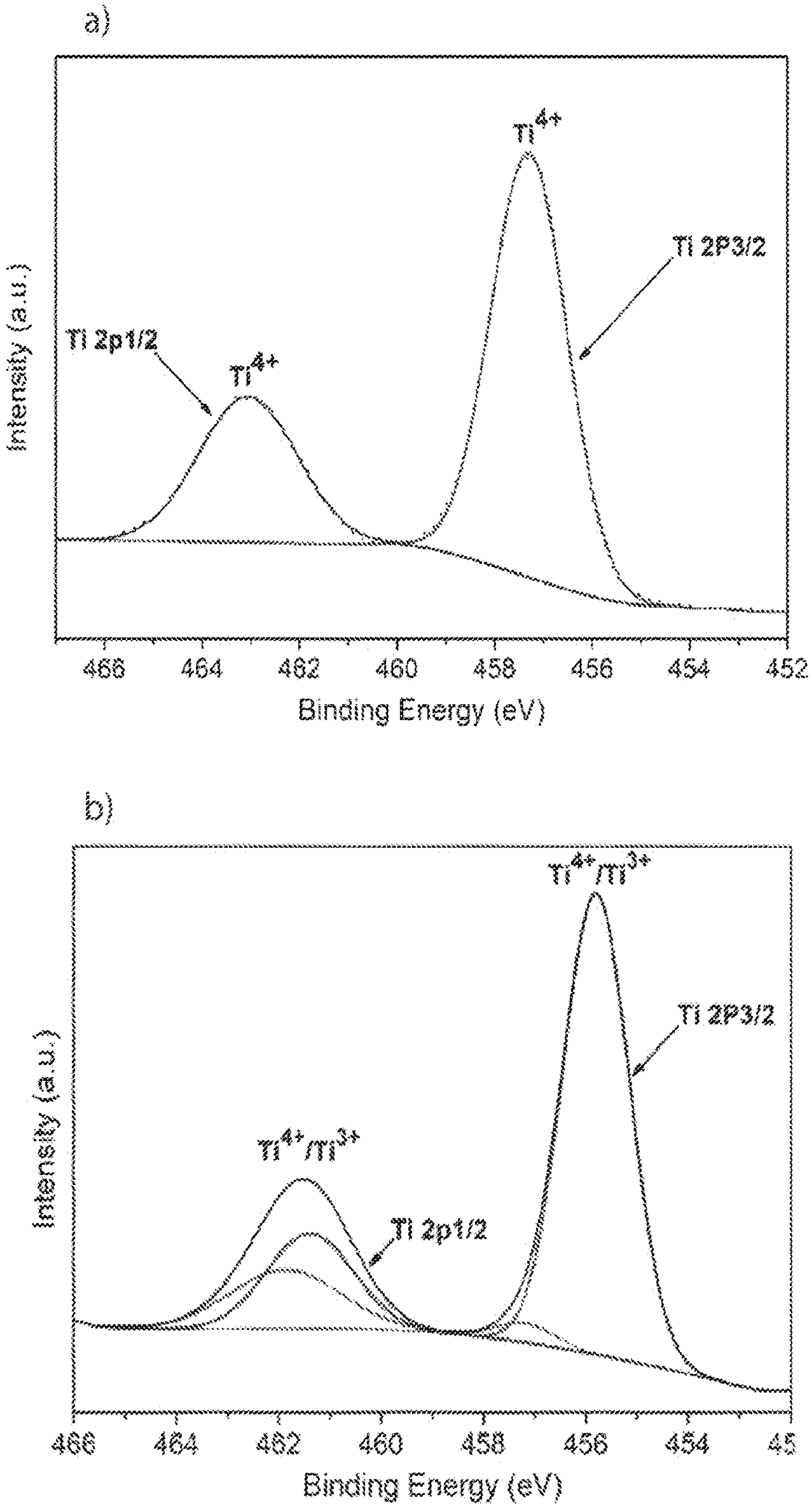
FIG. 10 shows the XPS analyses of the Ti 2p region after peak deconvolution and background removal for Commercial $TiO_2$ (a) and Modified-$TiO_2$ (b) according to the principles of the present invention.

The XPS analyses of the Ti 2p region after peak deconvolution and background removal for Commercial $TiO_2$ and Modified-$TiO_2$ are shown in FIG. 10. For Commercial $TiO_2$ two symmetric Gaussian distributions are observed (FIG. 10(*a*)). For Modified-$TiO_2$ two peaks of lower intensity are also observed, indicating the presence of lower valence states for Ti (FIG. 10(*b*)). The main peaks at 457.3 eV (Ti $2p_{3/2}$) and 463.2 eV (Ti $2p_{1/2}$) in Commercial $TiO_2$ are due to the presence of $Ti^{4+}$. The less intense peaks at 456.8 eV (Ti $2p_{3/2}$) and 460.9 eV (Ti $2p_{1/2}$) in Modified-$TiO_2$ indicate the presence of $Ti^{3+}$. The $Ti^{3+}/Ti^{4+}$ ratio was 12.3% and was calculated taking into account the total area of the deconvolutions in each region. The presence of $Ti^{3+}$ in Modified-$TiO_2$ indicates that the oxygen vacancies were generated to maintain the electrostatic balance according to the following equation:

$$4Ti^{4+}+O^{2-}\rightarrow 4Ti^{4+}+2e^{-}/X+0.5O_2$$

$$4Ti^{4+}+O^{2-}\rightarrow 2Ti^{4+}+2Ti^{3+}+X+0.5O_2$$

The "X" represents a vacant site originating from the removal of $O^{2-}$ from the $TiO_2$ matrix. It can be concluded that an oxygen vacancy is generated together with two $Ti^{3+}$ cations. Slight displacements of 1.5 eV are also observed in the main peaks of $TiO_2$ in Modified-$TiO_2$. From 457.3 eV (Ti $2p_{3/2}$) to 455.8 eV and from 463.2 eV (Ti $2p_{1/2}$) to 461.7 eV, due to the modification that takes place on the surface of the $TiO_2$ matrix when the oxygen vacancies are generated.

Figure 11:
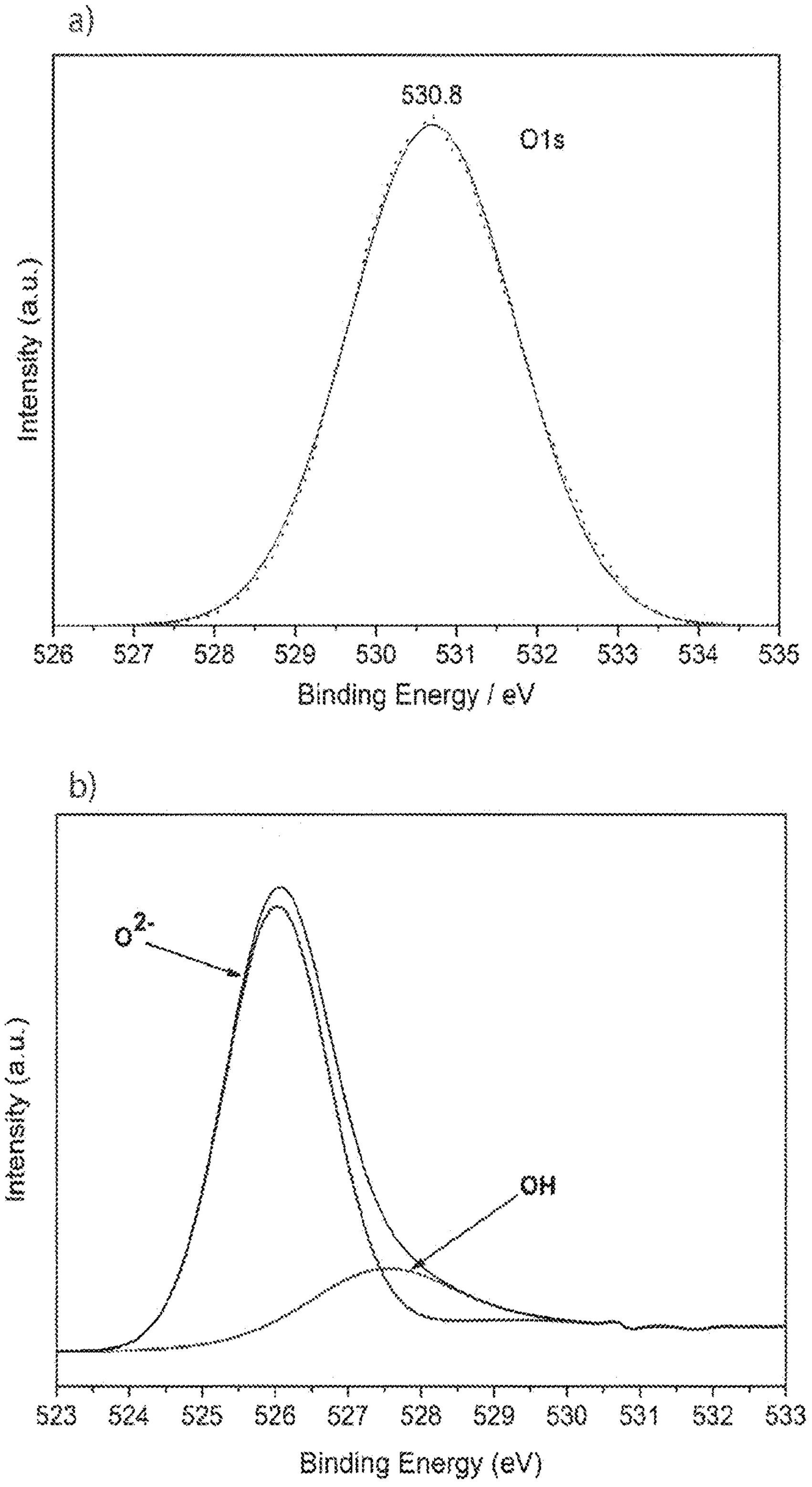
FIG. 11 shows the XPS analyses of the 0 is region after peak deconvolution and background removal for Commercial $TiO_2$ (a) and Modified-$TiO_2$ (b) according to the principles of the present invention.

Regarding the O 1s spectrum showed in FIG. 11, the binding energy at 530.8 eV in Commercial $TiO_2$ (FIG. 11(*a*)) and in Modified-$TiO_2$ (FIG. 11(*b*)) respectively, can be assigned to the oxygen bound to the $Ti^{4+}$ ions in Commercial $TiO_2$, while a small shoulder at 528 eV in Modified-$TiO_2$ implies that its surface is partially covered with $OH^-$ groups, proving the introduction of cobalt cations into the $TiO_2$ structure, confirming the XPS results for Ti 2p (FIG. 10).

Example 12

An essay was performed to study the thermal stability of the titanium-based bimetallic heterogeneous catalyst comprising a support of titanium dioxide doped with cobalt cations and transition metal nanoparticles impregnated in the support (Modified-$TiO_2$—Au—Co) of Example 3 according to the present invention, in comparison with a catalyst comprising a support of titanium dioxide doped with titanium (IV) cations and gold nanoparticles (ModifiedTiIV—$TiO_2$—Au) according to the prior art, by a thermogravimetric analysis (TGA).

Figure 12:
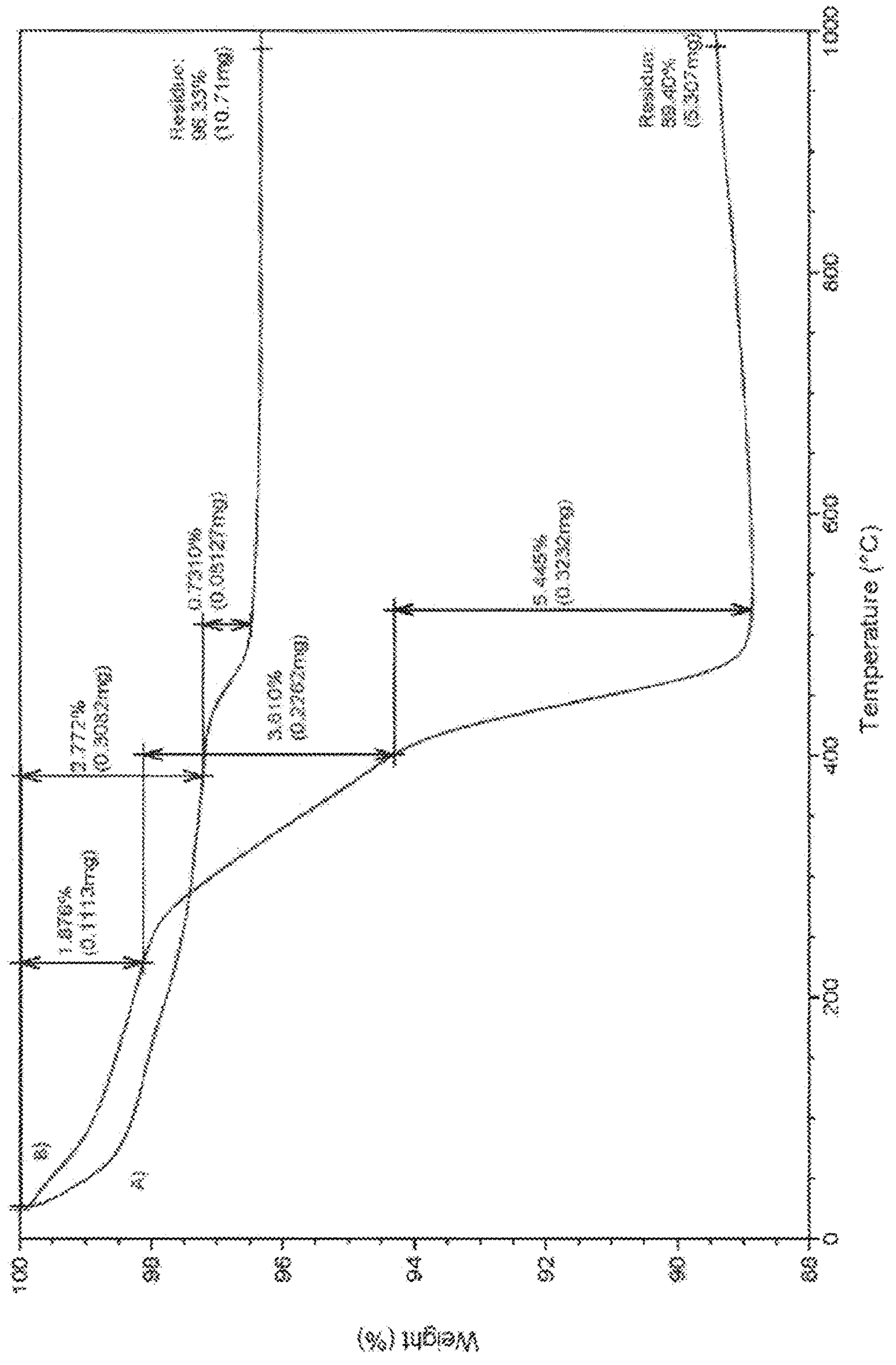
FIG. 12 shows a TGA for the Modified-$TiO_2$—Au—Co (A) according to the principles of the present invention and for the ModifiedTiIV—$TiO_2$—Au (B) of the prior art.

Both Modified-$TiO_2$—Au—Co and ModifiedTiIV—$TiO_2$—Au were subjected to a temperature ramp of 25-1000° C. (10° C./min). In FIG. 12 it is shown the TGA for the Modified-$TiO_2$—Au—Co (A), and two losses of mass can be observed, one of 2.7% at 59.42° C., which is associated with the loss of physisorbed water on its surface, and a second one of 0.97% at 436.74° C., which corresponds to the reduction of its metallic phase. The total loss of mass in thermal processes for the Modified-$TiO_2$—Au—Co is 3.67%, so the Modified-$TiO_2$—Au—Co is considered as highly stable during thermal processes, as the aldol condensation reaction of ethanol to butanol.

Also in FIG. 12 it is shown the TGA for the ModifiedTiIV—$TiO_2$—Au (B), and in this case three losses of mass can be observed, one of 1.873% at 90.48° C., which is associated with the loss of physisorbed water on its surface, a second one of 3.810% at 277.06° C., which is associated with the loss of physisorbed water in the pores of the material and organic matter from the urea used during the deposition of the gold nanoparticles with the Deposition-precipitation with Urea (DPU) method, and a third one of 5.445% at 473.29° C., which is associated with organic matter and carbonate groups formed on its surface derived from the use of urea during DPU method. The total loss of mass in thermal processes for the ModifiedTiIV—$TiO_2$—Au is 10.6%, so the ModifiedTiIV—$TiO_2$—Au is considered as moderately stable during thermal processes.

Example 13

An essay was performed to further assess the thermal stability of the titanium-based bimetallic heterogeneous catalyst comprising a support of titanium dioxide doped with cobalt cations and transition metal nanoparticles impregnated in the support (Modified-$TiO_2$—Au—Co) of Example 3 according to the present invention, in comparison with a catalyst comprising a support of titanium dioxide doped with titanium (IV) cations and gold nanoparticles (ModifiedTiIV—$TiO_2$—Au) according to the prior art, by a thermogravimetric analysis (TGA) over 20 catalytic cycles under the same conditions.

Figure 13:
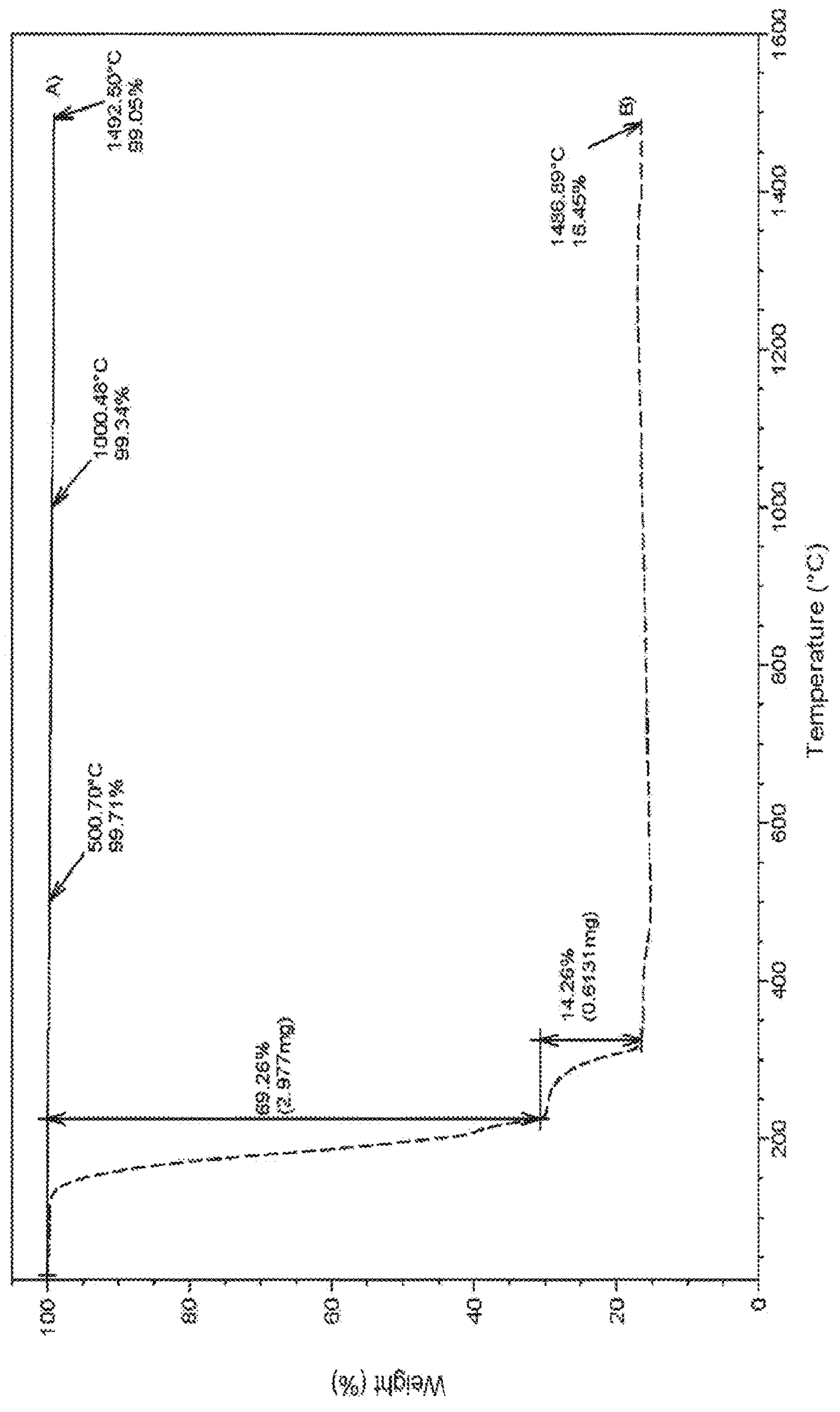
FIG. 13 shows a TGA over 20 catalytic cycles for the Modified-$TiO_2$—Au—Co (A) according to the principles of the present invention and for the ModifiedTiIV—$TiO_2$—Au (B) of the prior art.

In FIG. 13 it is shown the TGA for the Modified-$TiO_2$—Au—Co (A) as an average of the 20 catalytic cycles. During each catalytic cycle, 3 temperatures were tested: 500° C., 1000° C. and 1500° C. For the temperature of 500° C., a stability percentage of 99.68% was recorded, for 1000° C., a stability percentage of 99.34% was recorded, and for 1500° C. a stability percentage of 99.00% was recorded. The highest yield of butanol obtained during the aldol condensation reaction for the Modified-$TiO_2$—Au—Co was 96% at 250° C., which affirms that the Modified-$TiO_2$—Au—Co, according to the present invention, is a highly profitable catalyst for this process.

FIG. 13 shows the TGA for the ModifiedTiIV—$TiO_2$—Au (B) as an average of the 20 catalytic cycles. During each catalytic cycle, 3 temperatures were tested: 500° C., 1000° C. and 1500° C. As it can be observed in FIG. 13, each catalytic cycle provokes a loss of mass, associated with physisorbed and chemisorbed water and the decomposition of organic matter related to the DPU method, which poisons the catalyst. During the 20 catalytic cycles the stability percentage of the ModifiedTiIV—$TiO_2$—Au was 21.39%.

Example 14

An essay was performed to determine the vapor pressure and purity of the butanol obtained according to the process described in Example 8 during the aldol condensation from ethanol to butanol using the titanium-based bimetallic heterogeneous catalyst comprising a support of titanium dioxide doped with cobalt cations and transition metal nanoparticles impregnated in the support (Modified-$TiO_2$—Au—Co) of Example 3, according to the present invention.

In this essay, the vapor pressure (Reid) of the butanol was measured according to the ASTM D323-15a method in the facilities of the Mexican Institute of Petroleum. In this regard, the reported vapor pressure of the butanol obtained using Modified-$TiO_2$—Au—Co was 1.53 kPa, or 0.22 $lb/plg^2$.

On the other hand, purity was measured using gas chromatography-mass spectrometry (GC-MS) in the facilities of the Mexican Institute of Petroleum. In this regard, the reported purity was of 98.98%.

In accordance with the foregoing, it shall be apparent to a person skilled in the art that the preferred embodiment of the titanium-based bimetallic heterogeneous catalyst, its manufacturing process and the method for the production of butanol using the same illustrated above is set forth for illustrative purposes only but not limited to the present invention, since a person skilled in the art can make numerous variations thereto, provided they are designed according to the principles of the present invention. In fact, the titanium-based bimetallic heterogeneous catalyst could be used as a catalyst in any chemical reaction involving aldol condensation.

Accordingly, the present invention includes all of the embodiments that a person skilled in the art can pose from the concepts contained in the present specification, in accordance with the following claims.

The invention claimed is:

1. A titanium-based bimetallic heterogeneous catalyst comprising a support of titanium dioxide doped with cobalt cations, said support being impregnated with transition metal nanoparticles.

2. The titanium-based bimetallic heterogeneous catalyst according to claim 1, wherein the cobalt cations are cobalt, cobalt (II) and cobalt (III) or a mixture thereof.

3. The titanium-based bimetallic heterogeneous catalyst according to claim 1, wherein the cobalt cations are absorbed into the surface of the support of titanium dioxide.

4. The titanium-based bimetallic heterogeneous catalyst according to claim 1, wherein the transition metal nanoparticles are selected from cobalt (Co) nanoparticles, rhodium (Rh) nanoparticles, gold (Au) nanoparticles, copper nanoparticles (Cu) or a mixture thereof.

5. The titanium-based bimetallic heterogeneous catalyst according to claim 4, wherein the transition metal nanoparticles are a mixture of gold and cobalt nanoparticles, which forms a nanoalloy (Au—Co) in the surface of the titanium dioxide support.

6. The titanium-based bimetallic heterogeneous catalyst according to claim 1, wherein the transition metal nanoparticles are from 0.1 to 2.0% of the total weight of the titanium-based bimetallic heterogeneous catalyst.

7. The titanium-based bimetallic heterogeneous catalyst according to claim 6, wherein the transition metal nanoparticles are 0.5 to 1.5% of the total weight of the titanium-based bimetallic heterogeneous catalyst.

8. The titanium-based bimetallic heterogeneous catalyst according to claim 1, wherein the titanium dioxide support doped with cobalt cations is of a controlled geometry and low coordination.

9. The titanium-based bimetallic heterogeneous catalyst according to claim 1, wherein the average crystal size of the titanium dioxide support doped with cobalt cations is between nm and 100 nm.

10. The titanium-based bimetallic heterogeneous catalyst according to claim 1, wherein the specific surface area of the titanium dioxide support doped with cobalt cations is between 40 m2/g and 110 m2/g.

11. A manufacturing process of a titanium-based bimetallic heterogeneous catalyst comprising the following steps: a) mixing titanium dioxide with a cobalt salt to obtain a support of titanium dioxide doped with cobalt cations; b) adding to the support of titanium dioxide doped with cobalt cations at least one transition metal salt solution to obtain a titanium-based bimetallic heterogeneous catalyst comprising titanium dioxide doped with cobalt cations and transition metal nanoparticles impregnated in the support.

12. The manufacturing process of a titanium-based bimetallic heterogeneous catalyst according to claim 11, wherein the step of mixing titanium dioxide with a cobalt salt to obtain a support of titanium dioxide doped with cobalt cations is carried out by a wet precipitation process.

13. The manufacturing process of a titanium-based bimetallic heterogeneous catalyst according to claim 12, wherein the wet precipitation process is carried on in water.

14. The manufacturing process of a titanium-based bimetallic heterogeneous catalyst according to claim 11, wherein after the step of mixing titanium dioxide with a cobalt salt to obtain a support of titanium dioxide doped with cobalt cations the mixture is calcinated.

15. The manufacturing process of a titanium-based bimetallic heterogeneous catalyst according to claim 14, wherein the calcination is carried out at a temperature from 350 to 700° C. under air or hydrogen atmosphere.

16. The manufacturing process of a titanium-based bimetallic heterogeneous catalyst according to claim 11, wherein the titanium dioxide is a titanium dioxide with at least 70% of anatase crystalline phase.

17. The manufacturing process of a titanium-based bimetallic heterogeneous catalyst according to claim 11, wherein the cobalt salt is a phosphate, sulphate, acetate, citrate, chloride or a mixture thereof.

18. The manufacturing process of a titanium-based bimetallic heterogeneous catalyst according to claim 11, wherein the step of adding to the support of titanium dioxide doped with cobalt cations at least one transition metal salt solution is carried out by a wet precipitation process.

19. The manufacturing process of a titanium-based bimetallic heterogeneous catalyst according to claim 18, wherein the wet precipitation process is carried on in water.

20. The manufacturing process of a titanium-based bimetallic heterogeneous catalyst according to claim 11, wherein two transition metal salt solutions are added to the support of titanium dioxide doped with cobalt cations.

21. The manufacturing process of a titanium-based bimetallic heterogeneous catalyst according to claim 20, wherein a first transition metal salt solution is added to the support of titanium dioxide doped with cobalt cations to impregnate the support with nanoparticles of a first transition metal, and subsequently a second transition metal salt solution is added to the support of titanium dioxide doped with cobalt cations to impregnate the support with nanoparticles of a second transition metal.

22. The manufacturing process of a titanium-based bimetallic heterogeneous catalyst according to claim 21, wherein after adding the first metal transition salt solution, the mixture is dried and calcinated; and after the second metal transition salt solution is added and the mixture is calcinated again.

23. The manufacturing process of a titanium-based bimetallic heterogeneous catalyst according to claim 11, wherein each transition metal salt solution could be selected from a gold (Au) salt solution or a cobalt (Co) salt solution.

24. The manufacturing process of a titanium-based bimetallic heterogeneous catalyst according to claim 23, wherein the gold salt solution is HAuCl4 and the cobalt salt solution is a phosphate, sulphate, acetate, citrate, chloride or a mixture thereof.

* * * * *